United States Patent [19]

Mauldin et al.

[11] 4,378,793
[45] Apr. 5, 1983

[54] REMOVABLE ANKLE BRACE

[75] Inventors: Donald M. Mauldin; Richard E. Jones, III, both of Dallas, Tex.

[73] Assignees: Kenneth D. Driver, Dallas; Melvin L. Stills, Lewisville, both of Tex.; part interest to each

[21] Appl. No.: 266,966

[22] Filed: May 26, 1981

[51] Int. Cl.³ .............................................. A61F 3/00
[52] U.S. Cl. ................................. 128/80 H; 128/166
[58] Field of Search ................ 128/80 H, 80 R, 80 E, 128/80 F, 83, 84 R, 87 R, 89 R, 165, 166

[56] References Cited

U.S. PATENT DOCUMENTS

| | | |
|---|---|---|
| 1,575,042 | 3/1926 | Denniston ........................ 128/80 H |
| 2,278,626 | 4/1942 | Vasko . |
| 2,317,020 | 4/1943 | Banister . |
| 2,341,963 | 2/1944 | Telson . |
| 2,404,083 | 7/1946 | Murray . |
| 2,423,354 | 7/1947 | Vanhoesen . |
| 2,614,340 | 10/1952 | Larkin . |
| 2,725,648 | 12/1955 | Kirk et al. . |
| 2,733,522 | 2/1956 | Murray . |
| 2,762,367 | 9/1956 | Rubin . |
| 2,810,213 | 10/1957 | Jonas . |
| 2,875,752 | 3/1959 | Lovich . |
| 2,884,717 | 5/1959 | Goldberg . |
| 3,044,463 | 7/1962 | Cool . |
| 3,307,536 | 3/1967 | Blosser . |
| 3,545,104 | 12/1970 | Laurie . |
| 3,566,487 | 3/1971 | Beightol . |
| 3,584,402 | 6/1971 | Silverman . |
| 3,613,674 | 10/1971 | Volz . |
| 3,633,573 | 1/1972 | Lipson . |
| 3,802,424 | 4/1974 | Newell . |
| 3,805,773 | 4/1974 | Sichau ............................ 128/80 F |
| 3,814,088 | 6/1974 | Raymond ........................ 128/80 H |
| 3,905,135 | 9/1975 | Debusk . |
| 4,057,056 | 11/1977 | Payton ............................ 128/89 R |
| 4,178,925 | 12/1979 | Hirt . |
| 4,200,997 | 5/1980 | Scheinhaus . |
| 4,280,489 | 7/1981 | Johnson, Jr. ................... 128/80 H |

Primary Examiner—John D. Yasko
Attorney, Agent, or Firm—Richards, Harris & Medlock

[57] ABSTRACT

A removable ankle brace (10) is provided for stabilizing the ankle of a patient. A flexible cuff (12) is initially wrapped about the ankle and lower leg of the patient after injury or surgery. The purpose of the cuff is to cushion and protect the ankle. The remainder of the ankle brace is then positioned about the ankle and includes a post operative shoe (18) and left and right side members (14, 16) extending upwardly therefrom past the ankle to the lower leg of the patient. A contoured portion (60) is provided on each of the side members and shaped to fit the lower leg of the patient. Rigid metal ankle stays (62) are provided on each side member and extend upward from the postop shoe (18) adjacent the ankle to enhance the stabilization thereof. Buckles (86) are anchored to the metal stays and side pieces to secure the ankle brace about the ankle with straps (92). Buckles (86) are also anchored to the contoured portion (60) of each side member to secure the brace to the lower leg with straps (92). Flaps (100, 102) may be secured on opposite sides of the postop shoe (18) which cooperate with a buckle (108) and strap (106) to secure the foot on the inner sole (32) of the shoe. Cross straps (110) cross about the upper portion of the foot and are anchored to the metal ankle stays by buckles (84) to further secure the foot on the inner sole.

3 Claims, 8 Drawing Figures

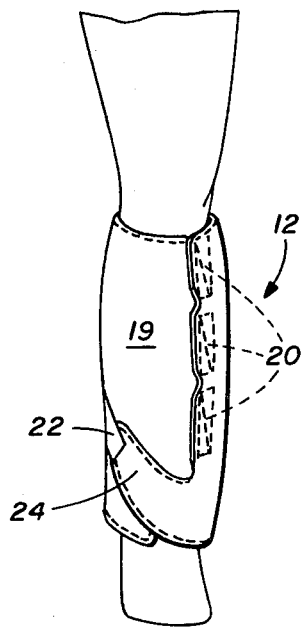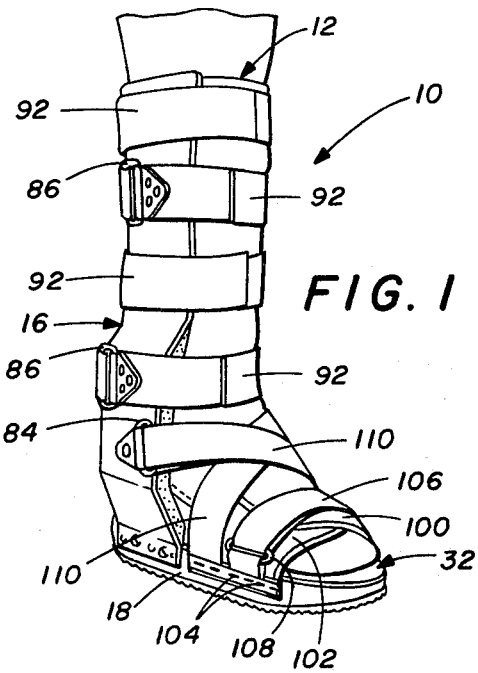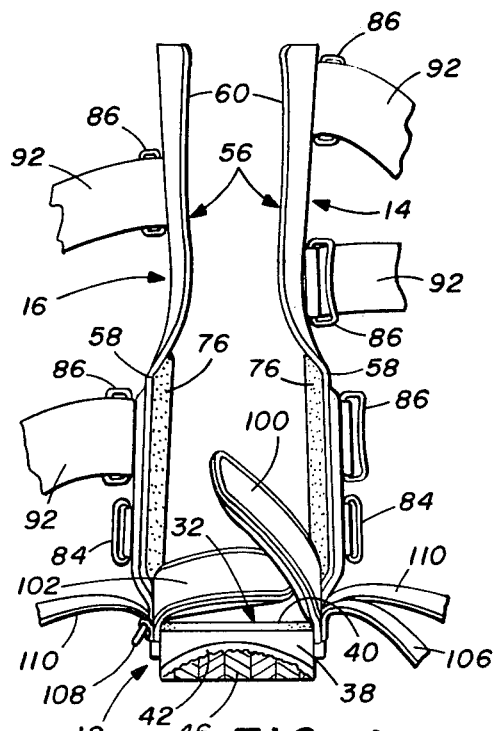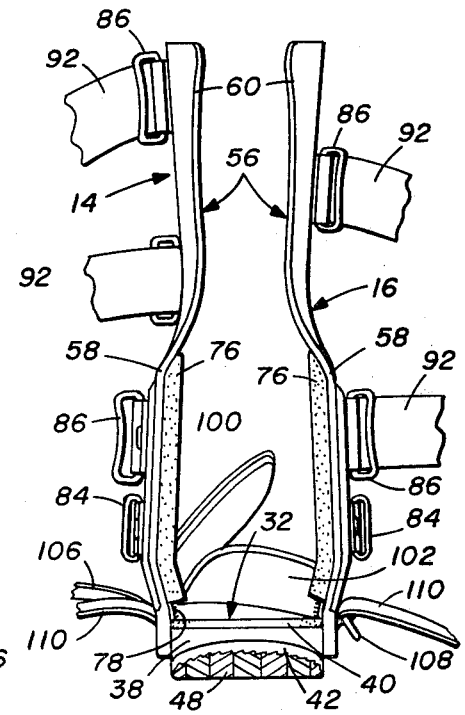

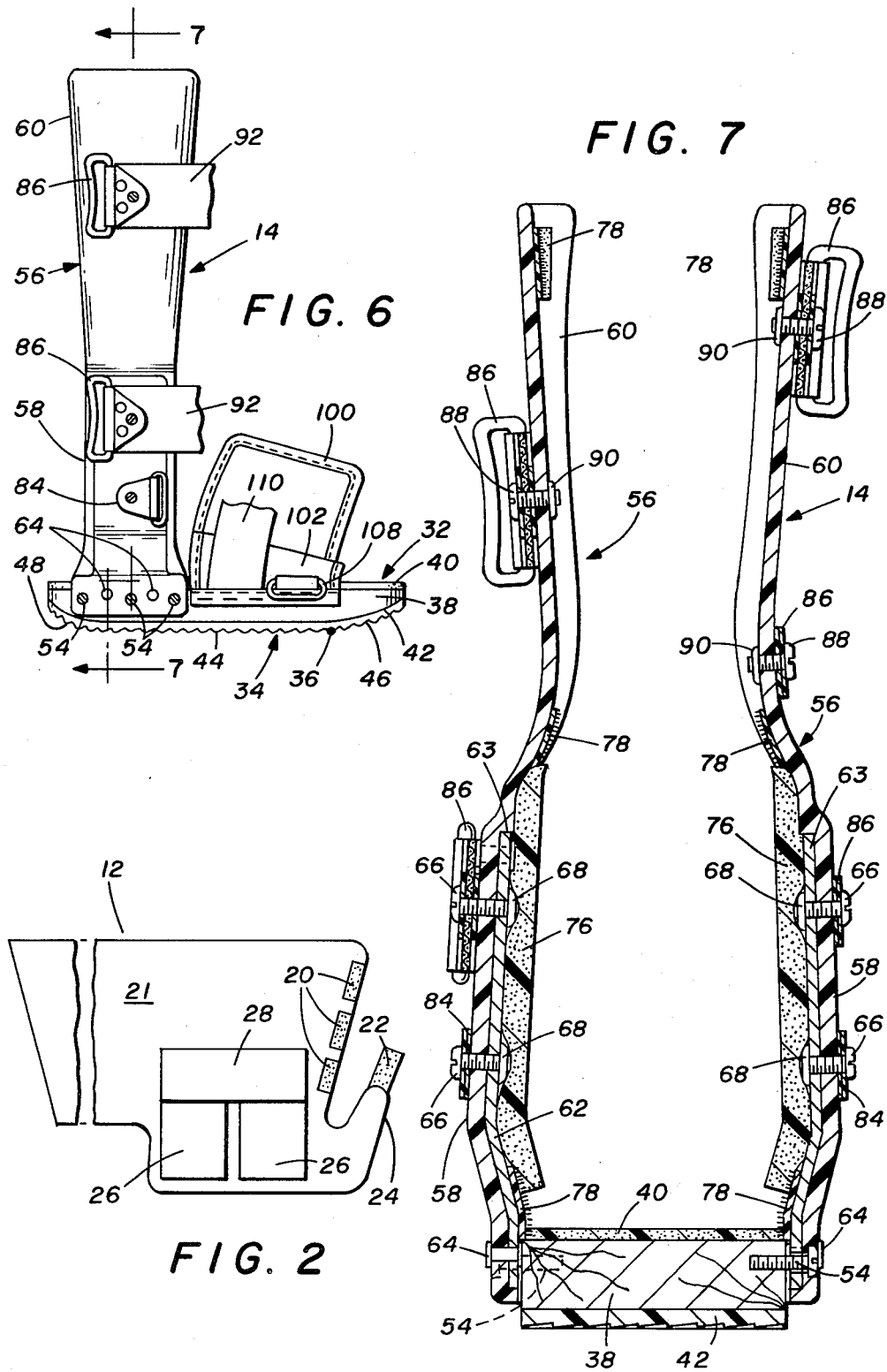

REMOVABLE ANKLE BRACE

TECHNICAL FIELD

This invention relates to care for the lower leg, and in particular, to stabilization of the ankle.

BACKGROUND ART

It is often necessary to immobilize the ankle and surrounding tissue in a foot after injury or surgery. In the past, plaster casts have been used which encapsulate the lower leg and foot of the patient to immobilize the ankle joint. These casts may be designed solely to stabilize the ankle or may include a metal stirrup to permit walking with the cast.

The placement of the cast on the ankle is a time-consuming and costly procedure. In addition, the ankle joint is commonly swollen when applying the cast. When the swelling is reduced, the cast then provides a poor fit to the ankle joint, reducing the effectiveness of the immobilization. In many cases, the area adjacent the ankle joint will bleed after the cast is applied. In most cases, the bleeding stops after a short while. However, the blood dried gauze within the cast must remain on the foot until the cast is removed, often weeks later. If bleeding persists, the cast must be removed from the condition to be corrected. This entails a second costly application of the cast.

During use of a plaster cast, it becomes virtually impossible to bathe in the normal manner. No technique has been discovered which will effectively prevent water from entering the cast. In addition, the confirming and rigid nature of the cast often leads to skin discomfort to the patient.

Another often used technique for ankle stabilization is the use of bandage wrapping. This technique permits ready removal for bathing or relief of irritation to the skin. However, the bandage does not provide rigid stabilization of the ankle and the patient must often walk with crutches to avoid the application of weight to the injured ankle.

Therefore, a need exists for an improvement in the art of stabilizing the ankle which combines the function of rigid stabilization of the ankle while permitting ready removal to permit the application of new bandages and allow the patient to bathe and relieve discomfort.

DISCLOSURE OF THE INVENTION

In accordance with the invention, a removable ankle brace is provided. The ankle brace includes an orthopedic shoe having an outer sole and a rigid flat inner sole for contacting the foot of the patient. A cuff is provided for wrapping about the ankle and lower leg. Left and right side members are rigidly secured on opposite sides of the orthopedic shoe and extend upward adjacent the ankle joint to the lower leg where the foot contacts the inner sole. Structure is provided for securing the forefoot on the inner sole of the orthopedic shoe. Structure is also provided to secure the cuff, and the left and right side members about the ankle and lower leg of the patient.

In accordance with another aspect of the invention, the removable ankle brace includes left and right metal plates secured to the orthopedic shoe and the left and right side members, respectively, adjacent the ankle joint.

In accordance with yet another aspect of the present invention, the removable ankle brace includes a cuff for wrapping about the ankle and lower leg of the patient and an orthopedic shoe having a rigid inner sole for contacting the foot of the patient and a rigid outer sole. The outer sole has first and second contact faces separated by a fulcrum, the first contact face being relatively flat and extending rearward of the fulcrum and the second contact face extending forward of the fulcrum and toward the inner sole. When the ankle brace is secured to the patient, the metatarsal point of the foot is supported on the inner sole forward of the fulcrum for initiating a rolling motion on the second surface as weight is shifted to the metatarsal point of the foot during walking. The ankle brace further includes left and right side members fastened on opposite sides of the orthopedic shoe and extending upward past the ankle joint to the lower leg. The left and right side members each have structure to secure the cuff thereto. The left and right side members also each have an offset portion adjacent the ankle joint. Metal stays are provided on either side of the ankle joint and are secured to the orthopedic shoe and the left and right side members. Adjustable toe straps are provided for securing the forefoot to the inner sole of the orthopedic shoe. Adjustable ankle straps are mounted to said left and right side members and metal plates for securing the left and right side members and cuff to the patient adjacent the ankle joint. Adjustable lower leg straps are fastened to the left and right side members for securing the left and right side members and cuff to the lower leg.

BRIEF DESCRIPTION OF THE DRAWINGS

A more complete understanding of the invention and its advantages will be apparent from the following Detailed Description taken in conjunction with the accompanying Drawings in which:

FIG. 1 is a perspective view of a removable ankle brace forming the present invention secured on a patient;

FIG. 2 is a plan view of a cuff used in the removable ankle brace;

FIG. 3 illustrates the cuff positioned on the ankle and lower leg of the patient;

FIG. 4 illustrates a front view of the ankle brace with the cuff removed;

FIG. 5 illustrates a back view of the ankle brace with the cuff removed;

FIG. 6 illustrates a side view of the ankle brace with the cuff removed;

FIG. 7 illustrates a vertical cross-sectional view of the ankle brace taken along line 7—7 in the direction of the arrows in FIG. 6.

DETAILED DESCRIPTION

Figure 8:
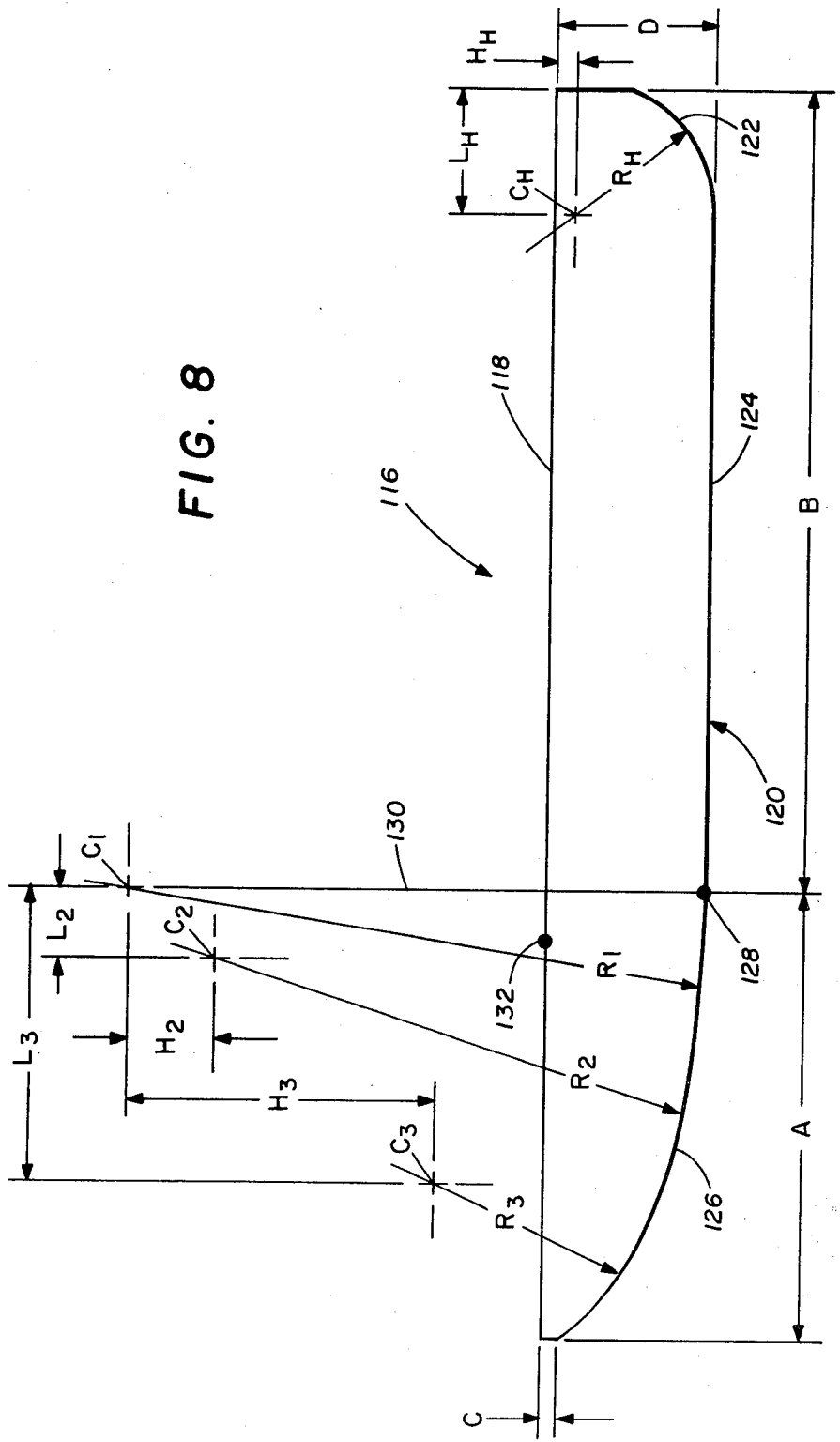
FIG. 8 is a side view of the postop shoe used in the removable ankle brace.

Referring now to the drawings, wherein like reference characters designate like or corresponding parts throughout several views, FIGS. 1-7 illustrate a removable ankle brace 10 comprising the present invention.

The ankle brace 10 includes several major components. A cuff 12 is wrapped about the ankle and lower leg of the patient. An integral unit including left side member 14, right side member 16 and postoperative (postop) shoe 18 are then positioned over the ankle and lower leg. The entire structure is maintained on the leg by use of a number of straps.

The removable ankle brace 10 may be used with a large range of lower leg and ankle sizes. In addition, it is designed to be removable at any time during treatment after injury or surgery and readily reattached. Finally, the brace 10 may be made of durable materials which permit the brace to be reused.

The cuff 12 is illustrated in greater detail in FIG. 2. The cuff 12 is to be in direct contact with the patient and is thus made of an appropriate material which allows the skin to breathe so that it will not macerate. The outer surface 19 of cuff 12 is preferably formed of a material having a plurality of minute loops receptive to engagement with a plurality of small hook-like members extending from an adjacent surface. A material of this type is sold under the trademark Velcro. Strips 20 are positioned along one edge of the cuff 12 and include the hook-like members permitting attachment to the outer surface 19 of cuff 12. Strips of this type are sold under the trademark Velcro. Strip 22, also having the hook-like members, is secured at the end of extension strap 24 of the cuff 12 as shown in FIG. 2.

Cushion pads 26 are attached to the inner surface 21 of the cuff 12 as shown in FIG. 2 by any suitable adhesive or other attachment means. A third cushion pad 28 is preferably positioned above cushion pads 26 as shown. When the cuff 12 is properly positioned about the ankle and lower leg of the patient as shown in FIG. 3, cushion pads 26 are positioned on either side of the ankle joint. Cushion pad 28 extends about the back of the heel and adjacent the ankle joint on both sides. Pads 26 and 28 are preferably formed of absorbent material so that any bleeding from the patient about the ankle region will be absorbed by the pads. This permits the pads to be replaced if necessary without the need to replace the entire cuff 12. As can be seen in FIG. 3, the strips 20 and 22 retain the cuff in its position about the ankle and lower leg of the patient in preparation for attachment of the members 14 and 16 and postop shoe 18.

The purpose of the postop shoe 18 is to provide a relatively rigid and planar inner sole 32 for supporting and preventing flexure of the foot of the patient while permitting the shoe 18 to roll on the rigid outer sole 34 forward of a fulcrum 36. Fulcrum 36 extends across the entire width of the shoe 18. The fulcrum is positioned so that when the foot of the patient is properly positioned on the shoe, the metatarsal point of the foot lies forward of the fulcrum. When the patient shifts his weight from the heel to the metatarsal point or ball of the foot, a rolling motion of the shoe 18 on the outer sole 34 forward of fulcrum 36 is initiated to provide a natural walking motion while maintaining the foot on the flat inner sole 32.

In the preferred embodiment, the desired function of the postop shoe 18 may be provided by including a rigid platform 38 having a planar upper surface and a lower surface having a planar portion and a curved portion. A flexible pad 40 is secured to the upper surface of the rigid platform to provide some cushioning to the foot of the patient and a nonslip pad 42 is securely attached to the lower portion of the platform 38 to prevent the patient from slipping. The rigid platform 38 may, for example, be constructed of wood and the nonslip pad 42 may be formed from a rubber-like material.

As can best be seen in FIG. 6, the outer sole 34 includes a relatively planar portion 44 extending rearward of fulcrum 36. This permits the patient to stand on a stable platform. A curved portion 46 extends forward of the fulcrum and toward the inner sole. A second curved portion 48 is provided at the heel. As the patient walks in a normal manner, the curved portion 48 will initially contact the ground, rolling the brace and lower leg of the patient onto the planar portion 44 as the weight of the patient is applied to the leg. As the weight of the body moves onto the metatarsal point, the shoe pivots about the fulcrum and onto the curved portion 46 to rotate the lower leg and brace to provide a natural striding motion to the leg while maintaining the foot on a planar surface.

The curved portion 48 is provided with a radius of curvature selected to provide a natural transition from supporting the weight of the body on planar portion 44 to the curved portion 46 as the shoe 18 pivots about fulcrum 36 and rolls onto curved portion 46. At the instant the weight of the body is shifted to the metatarsal region it initiates a rolling motion of the shoe from the fulcrum 36 along the curved portion 46. As the center of mass of the body continues to move anterior or forward of the weight bearing portion of the foot, the shoe 18 continues to roll along the curved portion 46 until the foot is lifted off the ground. As the shoe 18 rolls along the curved portion 46, the portion of the foot supporting the body weight is continuously changing. This avoids prolonged concentrations of stress on any part of the forefoot, particularly in the metatarsal region.

The curved portion 46 may have any curved or linear shape desired provided that the portion 46 forward of fulcrum 36 lies above the plane defined by the planar portion 44 and fulcrum 36 of the postop shoe 18. The portion of the inner sole 32 of postop shoe 18 forward of the fulcrum 36 must be of sufficient length to support the toes of the foot. In addition, the length of the inner sole 32 forward of the fulcrum 36 should not extend to a point where it would contact the walking surface as the shoe 18 pivots about fulcrum 36 before the degree of rolling motion on curved surface 46 equals the normal degree of pivotal motion about the metatarsal point of a foot in walking. It has been found that the entire range of human foot sizes encountered in normal circumstances will be accommodated by only four sizes of postop shoe 18.

The preferred construction of postop shoe 18 is illustrated in FIG. 8 and comprises a postop shoe 116. A planar sole 118 is provided which corresponds to inner sole 32. The outer sole 120 corresponds to outer sole 34 and has a curved heel portion 122 having a radius of $R_H$, a planar portion 124 and a curved portion 126. The curved portion 126 is formed of three curves of progressively shorter radii, $R_1$, $R_2$ and $R_3$ towards the toe of the shoe 116. The inner sole 118, outer sole 120 and inner connecting structure are formed of relatively rigid or semi-flexible material. The intersection of the planar portion 124 and curved portion 126 defines a fulcrum 128.

The foot is maintained and positioned on the inner sole 118 so that the metatarsal point of the foot is positioned forward of the fulcrum 128 and a vertical line 130 extending through the fulcrum. The metatarsal point of the foot may be positioned at point 132. In a typical application, point 132 may be positioned approximately ⅜ inch or one centimeter forward of line 130. The shoe 116 also serves to maintain a foot placed thereon in one position. This position does not significantly change during the walking motion as a result of the rigidity of the soles 118 and 120 of shoe 116.

The postop shoe 116 simulates the natural cyclical motion of the foot in walking. The curved portion 126 of shoe 116 consists of the three curves of progressively shorter radii which are blended together to form a smooth curve. This design is critical during the portion of the walking motion referred to as "heel off", which is the portion of the motion where the body weight is transferred to the metatarsal bones of the foot and the heel is lifted off the ground. When this portion of the walking motion occurs, this shoe 116 is forced into a gentle rolling action on curved portion 126, thereby avoiding a continued, localized area of stress that would occur in a flexible shoe. In normal walking, the heel of a foot is lifted slowly at first and more rapidly toward the end of the stance phase. The progressively shorter radii on the more forward or toeward parts of the curved portion 126 allow for the increased speed of rolling or elevation of the heel of the foot as the stance phase is completed. It is this continuous, smooth progression which allows the inner sole 118 of shoe 116 to stay with the foot and support it throughout the walking motion.

In a specific embodiment of the invention as illustrated in FIG. 8, shoes were constructed in a range of sizes, arbitrarily referenced as sizes 1 through 5, for use on feet which vary in size across a broad range. The dimensions listed below in Table 1 prove to be highly satisfactory for each of these sizes.

TABLE 1

| Size | A (in.) | B (in.) | C (in.) | D (in.) | $L_2$ (in.) | $L_3$ (in.) | $L_H$ (in.) |
|---|---|---|---|---|---|---|---|
| 1 | 3.25 | 6.50 | .125 | 1.125 | .50 | 2.10 | .875 |
| 2 | 3.50 | 6.625 | .125 | 1.125 | .50 | 2.32 | .875 |
| 3 | 3.75 | 7.25 | .125 | 1.125 | .58 | 2.40 | .875 |
| 4 | 4.00 | 7.75 | .125 | 1.125 | .72 | 2.68 | 1.0 |
| 5 | 4.25 | 8.06 | .125 | 1.125 | .44 | 2.44 | 1.0 |

| Size | $H_2$ (in.) | $H_3$ (in.) | $H_H$ (in.) | $R_1$ (in.) | $R_2$ (in.) | $R_3$ (in.) | $R_H$ (in.) |
|---|---|---|---|---|---|---|---|
| 1 | 1.55 | 4.95 | .125 | 6.71 | 5.11 | 1.38 | 1.0 |
| 2 | 4.22 | 8.30 | .125 | 10.18 | 5.92 | 1.45 | 1.0 |
| 3 | 6.62 | 11.37 | .125 | 13.32 | 6.72 | 1.62 | 1.0 |
| 4 | 9.18 | 13.76 | .125 | 15.95 | 6.75 | 1.76 | 1.0 |
| 5 | 9.15 | 14.95 | .125 | 18.05 | 8.91 | 2.78 | 1.0 |

The left and right side members 14 and 16 are rigidly secured on either side of the postop shoe 18 adjacent the heel of the shoe. As shown in FIG. 7, the side members may be secured to the platform 38 by screws 54. Each of the side members is substantially identical in construction, which increases the versatility of the brace. Therefore, only one will be described in detail.

The left side member 14 includes a semirigid side piece 56 which extends from the postop shoe 18 upward past the ankle and adjacent the lower leg of the patient when the brace is applied. The side piece 56 includes an offset portion 58 adjacent the ankle and a contoured upper portion 60 to conform to the shape of the lower leg or calf of the patient. In the preferred embodiment, the side piece 56 is formed of a moldable material, such as plastic.

A rigid ankle stay 62 is securely fastened to the inside of side piece 56 at the postop shoe 18 and adjacent the ankle of the patient. The side piece 56 preferably includes an inset 63 on its inner surface to accept the stay 62 as best shown in FIG. 7. The side piece 56 and stay 62 are attached by rivets 64 adjacent postop shoe 18 in the preferred embodiment. The stay 62 extends between the side piece 56 and postop shoe 18 so that screws 54 also act to secure the stay to the piece 56. Side piece 56 and stay 62 are secured together by threaded screws 66 and nuts 68 adjacent the ankle. In the preferred embodiment, the stay 62 is formed of stainless steel, steel or other rigid metal. The purpose of stay 62 is to provide great stability to the region about the ankle when the brace 10 is mounted on the patient. The side piece 56 is semirigid so that it may conform to the lower leg of the wearer without excessive chafing of the leg.

A cushion 76 is secured to the inner surface of the stay 62 and side piece 56 by any suitable adhesive to cushion the ankle. Distributed along the inner surface of the side piece 56 are a number of strips 78 having a plurality of hook-like members thereon. Again, the strips 78 may comprise material sold under the trademark Velcro. The strips 78 are used to secure the cuff 12 to the side member 14 to prevent movement of the cuff after the brace 10 has been applied to the lower leg.

The screws 66 and nuts 68 are also employed to secure buckles 84 and 86 to the outer surface of the side piece 56 adjacent the ankle. One or more threaded screws 88 and nuts 90 are employed in the contoured upper portion 60 of the side members to mount other buckles 86.

Straps 92 are provided to secure the side members and ankle brace 10 on the patient by positioning the straps as shown in FIG. 1. Each of the straps preferably includes sections having a plurality of minute loops and segments having a plurality of flexible hook-like members for attachment to the loop material. Again, the material of the straps may comprise Velcro. In the preferred embodiment, three straps 92 are provided on the upper portion 60 of the side members to secure the brace 10 about the lower leg of the patient. One strap 92 is provided on the offset portion 58 of the side members to secure the brace 10 about the ankle of the patient.

Flaps 100 and 102 are secured on either side of the postop shoe 18 forward of the side members. When the brace 10 is secured to the patient, the forefoot and toes of the patient's foot lie adjacent the flaps 100 and 102. In the preferred embodiment, the flaps may be constructed of any flexible material, such as leather. The flaps may be secured to the postop shoe 18 by any suitable method, such as staples 104. A toe strap 106 is secured near the forward portion of flap 100 for cooperation with buckle 108 secured adjacent the forward portion of flap 102. The strap 106 and buckle 108 permit the flaps to be secured over the forefoot and toes of the patient to comfortably but, rigidly, secure the forefoot on the inner sole 32. Again, the strap 106 preferably has sections having a plurality of loops and sections having a plurality of hook-like members to secure the strap 106 in the desired position.

Cross straps 110 are secured at the rear portions of both flaps 100 and 102 for cooperation with the buckle 84 on the opposite side of the brace 10. Again, the cross straps 110 include sections with a plurality of loop and hook-like portions to secure the cross straps in the desired position. The cross straps 110 and buckles 84 act to secure the top portion of the foot of the patient to the inner sole 32 to further stabilize the ankle region.

It will be readily apparent from the description above and the accompanying figures that ankle brace 10 comprises a significant improvement in devices for stabilizing the ankle. When the ankle is to be stabilized after injury or surgery, the cuff 12 is initially applied as shown in FIG. 3 and described hereinabove. The side members 14 and 16 and postop shoe 18 are then applied about the cuff on the lower leg and foot of the patient and secured thereto by straps 92, 106 and 110.

The adjustability of the straps permit the brace 10 to be used on many different patients. The brace has also been designed to be readily adapted to either the left or right leg. The ankle brace 10 may be adapted to an even greater range of leg sizes by providing cuffs 12 of varied dimensions.

While ankle brace 10 is readily applied to the patient, the brace may also be removed at any time during treatment and readily reapplied as needed. The brace may even be kept by the patient for reuse if the patient is again injured.

Although only one embodiment of the present invention has been illustrated in the accompanying drawings and described in the foregoing Detailed Description, it will be understood that the invention is not limited to the embodiment disclosed, but is capable of numerous rearrangements, modifications and substitutions of parts and elements without departing from the scope and spirit of the invention.

We claim:

1. A removable ankle brace for stabilizing the ankle of patient comprising:

a rigid shoe having a planar upper surface for engaging the sole of the patient's foot, side walls extending perpendicularly to the upper surface and downwardly therefrom, and an outer sole comprising the lowermost surface of the shoe;

the outer sole of the shoe having a fulcrum, a planar first portion extending rearwardly from the fulcrum to the heel of the shoe and a second portion comprising a continuous curve extending from the fulcrum upwardly and forwardly to the toe of the shoe;

means for locating the foot of the patient on the planar upper surface of the shoe with the metatarsal point of the foot positioned forward of the fulcrum so that the shoe normally sets on the planar first portion of the outer sole and pivots about the fulcrum onto the curved second portion as the weight of the patient shifts forward of the metatarsal point of the foot;

left and right side members positioned on opposite sides of the shoe and each including a thermoplastic side piece and a metal ankle stay;

the metal ankle stay of each side member engaging the adjacent side wall of the shoe and extending upwardly therefrom beyond the ankle of the patient;

the thermoplastic side piece of each side member surrounding the metal ankle stay thereof on the front, on the outside, and on the rear and extending upwardly from the shoe in contact with the metal ankle stay;

means securing the metal ankle stay of each side member to the side piece thereof;

a plurality of fasteners extending through the metal ankle stay and the thermoplastic side piece of each side member and into the adjacent side wall of the shoe for rigidly securing the side members to the shoe;

the metal ankle stay and the thermoplastic side piece of each side member comprising a first portion secured to the side wall of the shoe, a second portion extending from the upper end of the first portion angularly upwardly and outwardly with respect thereto and a third portion extending upwardly from the upper end of the second portion substantially parallel to the first portion;

the metal ankle stay of each side member terminating at the upper end of the third portion thereof;

the thermoplastic side piece of each side member further including a fourth portion extending from the end of the third portion angularly upwardly and inwardly with respect thereto and a fifth portion extending upwardly from the upper end of the fourth portion generally parallel to the first and third portions;

the fifth portion of each side piece being positioned over the first portion thereof and being curved inwardly to conform to the calf of the patient;

each side member further including a layer of foam padding secured to the inside surface thereof and extending upwardly along the inner surfaces of the second and third portions of the metal ankle stay and the thermoplastic ankle piece; and fastening means for securing the shoe and the side members to the foot and the calf of the patient, respectively.

2. The removable ankle brace according to claim 1 further including a foam cuff dimensioned to surround the ankle and the lower leg of the patient, and means mounted on the inner surfaces of the side members for securing the cuff thereto.

3. The removable ankle brace according to claim 1 wherein the fastening means comprises:

first strap means for connection between aligned points on the side walls of the shoe adjacent the toe thereof;

second strap means for connection between points on the side walls and points on the opposite side members;

said first and second strap means for securing the shoe to the foot of the patient; and third strap means for connection between aligned points on the side members to secure the side members to the calf of the patient.

* * * * *